United States Patent
Steeley et al.

(10) Patent No.: US 11,679,285 B2
(45) Date of Patent: Jun. 20, 2023

(54) ORGANIC AND MINERAL HYBRID SUNSCREEN SPRAY

(71) Applicant: L'OREAL, Paris (FR)

(72) Inventors: Kristin Gilida Steeley, Branchburg, NJ (US); Jaimie Mecca, Clifton, NJ (US); Patricia Brieva, Manalapan, NJ (US); Anil Shah, East Windsor, NJ (US)

(73) Assignee: L'OREAL, Paris (FR)

( * ) Notice: Subject to any disclaimer, the term of this patent is extended or adjusted under 35 U.S.C. 154(b) by 28 days.

(21) Appl. No.: 16/586,826

(22) Filed: Sep. 27, 2019

(65) Prior Publication Data

US 2021/0093547 A1 Apr. 1, 2021

(51) Int. Cl.
*A61Q 17/04* (2006.01)
*A61K 8/06* (2006.01)
*A61K 8/27* (2006.01)
*A61K 8/37* (2006.01)
*A61K 8/891* (2006.01)

(52) U.S. Cl.
CPC ............... *A61Q 17/04* (2013.01); *A61K 8/062* (2013.01); *A61K 8/27* (2013.01); *A61K 8/37* (2013.01); *A61K 8/891* (2013.01); *A61K 2800/596* (2013.01)

(58) Field of Classification Search
CPC .......... A61K 8/891; A61K 8/062; A61K 8/37; A61K 8/27; A61Q 17/04
See application file for complete search history.

(56) References Cited

U.S. PATENT DOCUMENTS

| | | | |
|---|---|---|---|
| 9,820,920 B2 | 11/2017 | Nikitczuk et al. | |
| 2011/0182834 A1* | 7/2011 | Do | A61K 8/0233 424/59 |
| 2014/0186411 A1* | 7/2014 | Shah | A61K 8/891 424/401 |

OTHER PUBLICATIONS

Aikens, P., Szabados, Z. (Mar. 2015). Formulating with Zinc Oxide. Creations Newsletter, Issue 3, 1-5. Retrieved from http://creationsnewsletter.com/issue3/3.aspx (Year: 2015) (Year: 2015).*
Babyganics Mineral-Based Sunscreen spray: https://babyganics.com/products/mineral-based-sunscreen-spray-50spf-2/; website last visited Sep. 20, 2019.
Dr. Dennis Gross, Sheer Mineral Sun Spray: https://drdennisgross.com/skincare/skin-concern/sun-protection-1/sheer-mineral-sun-spry-spf-50.html; website last visited Sep. 20, 2019.

* cited by examiner

*Primary Examiner* — Bethany P Barham
*Assistant Examiner* — Barbara S Frazier
(74) *Attorney, Agent, or Firm* — McNees Wallace & Nurick LLC

(57) ABSTRACT

A sunscreen composition is provided as a metastable oil-in-water emulsion that includes aqueous and oil phases, including a UV filter system that includes at least one of each of mineral UV filters and organic UV filters; an emulsification system that includes at least one ionic surfactant, at least one surfactant having a high HLB, and at least one surfactant having a low HLB, and at least one anionic emulsifier; and a solvent system that includes one or a combination of emollients and silicones.

20 Claims, No Drawings

ORGANIC AND MINERAL HYBRID SUNSCREEN SPRAY

FIELD OF THE INVENTION

The present disclosure is directed to skin care compositions that provide UV protection, in particular that can be delivered in a spray formulation.

BACKGROUND OF THE INVENTION

The photoprotection of keratinous substrates, including both skin and hair, is considered by many to be necessary in order to facilitate protection from sun-damage, sunburn, photo-aging, as well as to decrease the chances of skin cancer development caused by exposure to ultraviolet ("UV") radiation.

It is an object of the present disclosure to provide a sunscreen composition, in some particular embodiments a pump sprayable sunscreen composition, that provides SPF properties employing a UV filter system and that is formulated for aesthetically pleasing application to the skin. Currently marketed sprayable sunscreen sprays are typically oil-based water-in-oil compositions that may include one or more of pressurized propellants and alcohol-based formulas. It is well known that products containing alcohols require special safety measures to be taken during production, storage, and transport. In addition, alcohol-containing products are potentially flammable during use. As a result, alcohol-free products are preferred by consumers because of odor, tolerance, and safety considerations. Compositions that are formulated in the form of oil-in-water emulsions, including metastable formulations, avoid some of the challenges of alcohol solubilized water-in-oil compositions, however, providing aesthetically pleasing oil-in-water emulsions with acceptably high amounts of UV agents is not easily achieved. There are metastable products on the market that promise lighter textures than the heavier water-in-oil compositions and are more similar to water-in-oil compositions that include alcohol, but these formulae rely on high loads of cyclosiloxanes and other silicones to obtain fluidity and can be greasy. Furthermore, such compositions rely on thickeners for stabilization, and can be prone to agglomeration and whitening when applied to skin. Thus, there is a need for light oil-in-water sunscreen formulations that employ suitably high amounts of UV filters, do not suffer from tackiness, opacity, and poor spreadability, and are suitable for spray applications.

The present disclosure provides a light sprayable sunscreen composition that is pleasant to the touch with good spreadability. The composition includes separate oil and water phases that provide a meta-stabilized oil-in-water emulsion upon agitation at the time of application.

BRIEF SUMMARY OF THE INVENTION

In accordance with various embodiments, provided is a sunscreen composition that is a metastable oil-in-water emulsion that includes aqueous and oil phases. The composition includes a UV filter system that includes at least one of each of mineral UV filters and organic UV filters. The composition also includes an emulsification system that includes at least one ionic surfactant, at least one surfactant having a high Hydrophilic-Lipophilic Balance ("HLB"), and at least one surfactant having a low HLB, and at least one anionic emulsifier. The composition also includes a solvent system that includes one or a combination of emollients and silicones.

The oil phase includes the organic UV filters, and one or more oils, esters and dimethicones and oil phase solvents, and the aqueous phase includes water, surfactants and hydrating agents and other water phase components.

In some embodiments of the sunscreen composition, the components of the aqueous phase and the components of the oil phase, respectively, are present in the composition at a weight ratio of aqueous components to oil components in a range from about >1:1.

In some embodiments of the sunscreen composition, a phase ratio of the aqueous phase to the non-aqueous phase is calculated based on the weight of water to the weight of non-aqueous components that include the one or more oils, esters and dimethicone, and the organic UV filters present in the composition, wherein the phase ratio of the water and oil/ester/dimethicone components is from about 1.0 to about 2.0.

In some embodiments of the sunscreen composition, the phase ratio of the water to oil/ester/dimethicone components is from about 1.4 to 1.6.

In some embodiments of the sunscreen composition, each of mineral UV filters and organic UV filters is present in the system at a weight ratio of mineral to organic of 12:14-17, based on the total weight of the UV filter system.

In some embodiments of the sunscreen composition, the weight ratio of inorganic/mineral:organic UV filters is in the range from about 1:1 to about 1:1.5, or from about 1:1.15 to about 1:1.5.

In some embodiments of the sunscreen composition, the UV filter system is present in the composition in the range from about 15% to about 35% based on the total weight of the composition.

In some embodiments of the sunscreen composition, the UV filter system includes a UV filter comprising Zinc Oxide present in an amount in the range from about 8% to about 17%, and an organic UV filter comprising Homosalate present in an amount in the range from about 9% to about 12% and Octisalate present in an amount in the range from about 0.001% to about 5%, each present by weight based on the weight of the composition.

In some embodiments of the sunscreen composition, the UV filter system includes a UV filter comprising Zinc Oxide 12% and an organic UV filter comprising one or both of Homosalate present in an amount from about 9% to about 12%, and Octisalate present in an amount up to and including about 5%, each present by weight based on the weight of the composition.

In some embodiments, the sunscreen composition also includes at least one SPF booster.

In some embodiments, the SPF booster is selected from Ethylenediamine/Stearyl Dimer Dilinoleate Copolymer, Butyloctyl Salicylate, and Dimethicone and Acrylates/Dimethicone Copolymer, a styrene/acrylates copolymer, and a silicone polymer comprising dimethicone (and) dimethicone/vinyl dimethicone crosspolymer, and combinations of these.

In some embodiments, the SPF booster comprises a silicone film former comprising Ethylenediamine/Stearyl Dimer Dilinoleate Copolymer present from about 0.1% to about 5.0%, by weight based on the weight of the composition.

In some embodiments, the composition has an SPF of 30 to 50. In some embodiments, the SPF is 40.

The present invention is also directed to a method of inhibiting UV radiation from contacting a keratinous substrate by applying the above-disclosed sunscreen composition onto a surface of the keratinous substrate.

DETAILED DESCRIPTION OF THE INVENTION

The present disclosure provides a light sprayable sunscreen composition that is pleasant to the touch with good spreadability. The composition includes separate oil and water phases that provide a meta-stabilized oil-in-water emulsion upon agitation at the time of application. The inventors have provided a composition that provides the unexpected features of providing a flowable galenic suitable for spray application with high amounts of inorganic filters and providing an SPF in the range from 30 to 50, and in some embodiments, 40.

The term "Hydrophilic-Lipophilic Balance" or "HLB," refers to an empirical expression for the relationship of the hydrophilic and hydrophobic groups of a surfactant. This term is well known to those skilled in the art. See, e.g., "The HLB system. A time-saving guide to Emulsifier Selection" (Pub: ICI Americas Inc., 1984) and US2006/0217283 at [0053]. "High HLB" for an emulsifying surfactant in an O/W emulsion of the invention means an HLB of equal to greater than about 15. "Low HLB" for an emulsifying surfactant for an oil-in-water emulsions (O/W) emulsion of the invention means an HLB less than about 15. The HLB system is particularly useful to prepare O/W and water-in-oil emulsions (W/O) wherein it is customarily understood that W/Os often employ low HLB surfactants, having an HLB value of equal to or less than 6 and O/Ws often employ high HLB surfactants having an HLB value equal to or greater than 9. The total HLB of surfactants can be calculated by taking the weight percent of each surfactant of the surfactant mixture and multiplying the weight percent by the HLB to obtain a contribution of each individual surfactant on the HLB. The individual contributions are then added together to obtain the total HLB of the surfactant mixture. HLBs for individual surfactants can be found in well-known literature in the art or may be provided by a surfactant supplier. For example, if the surfactant mixture is a 50/30/20 blend of polysorbate 61, octyldodecyl xyloside and glyceryl stearate the total HLB of the 50/30/20 surfactant mixture is 7.11, wherein the HLB of polysorbate 61 is 9.4, the HLB of octyldodecyl xyloside is 5.5, and the HLB of glyceryl stearate 3.8. The contribution of polysorbate 61 is 0.5× 9.4=4.7. The contribution of octyldodecyl xyloside is 0.3× 5.5=1.65. The contribution of glyceryl stearate is 0.2× 3.8=0.76. The total HLB is 4.7+1.65+0.76=7.11.

The phrase "metastable" refers generally to a fluid, metastable formulation that can, after time, have a slight separation on the surface but can be remixed/re-emulsified with shaking.

"SPF booster" refers to a material which increases the UV absorption of another material when the two are intermixed in a composition by refracting UV radiation, thereby increasing the effective path length of the UV radiation through the composition. All SPF and UV-A ratings are provided on the basis of in-vivo value unless otherwise indicated.

Provided herein is a light sprayable sunscreen composition that is pleasant to the touch with good spreadability. The composition includes separate oil and water phases that provide a meta-stabilized oil-in-water emulsion upon agitation at the time of application.

In accordance with the various embodiments, the compositions are provided as a metastable oil-in-water emulsion, wherein the discrete phases that include the aqueous/water soluble components and the non-aqueous/water insoluble components are each present in the composition at a weight ratio of aqueous to non-aqueous in a range from about 1:1 to about >1:1.

In some embodiments, the ratio of the aqueous phase to the non-aqueous phase may be calculated by dividing the total weight of water by the total weight of the non-aqueous components that include oils, esters and dimethicone, and the organic UV filters, wherein the phase ratio of the water and oil/ester/dimethicone and organic UV filter components is from about 1.0 to about 2.0, or about 1.1 to about 1.9, or, about 1.2 to about 1.8, or about 1.3 to about 1.7, or about 1.4 to 1.6 or about 1.5.

UV Filter System

The composition according to the disclosure includes one or more inorganic or mineral based UV filter and one or more organic UV filter.

UV sun filters, active in UV-A and/or UV-B regions, used for the present invention can be water-soluble, fat-soluble or insoluble in commonly used cosmetic solvents. In some exemplary embodiments, the UV sun filters are selected from oil soluble UV sun filters. UV-A filters comprise groups of compounds which absorb light predominantly in the range of wavelengths 400 nm to 320 nm (UV-A) and UV-B filters comprise groups of compounds which absorb light predominantly in the range of wavelengths 400 nm to 320 nm 320 nm to 280 nm (UV-B). According to an embodiment of the invention, UV-A and UV-B can be two separate UV filters or they can be one UV filter with both UV-A and UV-B sun protection factor.

Examples of suitable UV filters include, but are not limited to, UV filters that are active in UV-A and/or UV-B regions, that may be water-soluble, fat-soluble or insoluble in commonly used cosmetic solvents, and may be inorganic or organic. UV-A filters comprise groups of compounds which absorb light predominantly in the range of wavelengths 400 nm to 320 nm (UV-A) and UV-B filters comprise groups of compounds which absorb light predominantly in the range of wavelengths 400 nm to 320 nm 320 nm to 280 nm (UV-B). According to an embodiment of the disclosure, UV-A and UV-B can be two separate UV filters or they can be one UV filter with both UV-A and UV-B sun protection factor.

The UV filter system includes a combination of inorganic/mineral based UV filters and organic UV filters.

In some embodiments, the UV filter system includes zinc oxide and one or more organic UV sun filters. In some embodiments, the organic UV filter may be selected from one or more of homosalate, octisalate (ethylhexyl salicylate), oxybenzone (benzophenone-3), mexoryl xl (drometrizole trisiloxane), and combinations of these. In some embodiments the compositions include a mixture of at least two or more of organic UV sun filters selected from octisalate, homosalate, oxybenzone, mexoryl xl. And in some particular embodiments, the UV filter system includes one or both homosalate and octisalate.

In accordance with the disclosure, a UV filter system is present in the composition in the range from about 15% to about 35% based on the total weight of the composition. In accordance with the various embodiments, the amount of each UV filter present in the compositions can range from about 1% to about 15%, or from about 2% to about 12%, or from about 3% to about 10% or any suitable combination, sub-combination, range, or sub-range thereof by weight, based on the weight of the composition. One of ordinary skill in the art, however, will appreciate that other ranges are within the scope of the invention.

In some particular embodiments, the amount of an inorganic/mineral UV filter is present in the composition in the range of from about 8% to about 17%, or from about 9% to about 15%, or from about 10% to about 14%, or from about 11% to about 13%, or at about 12%, or any suitable combination, sub-combination, range, or sub-range thereof by weight, based on the weight of the composition. In some particular embodiments, the UV filter system includes an inorganic UV filter comprising zinc oxide present in an amount that is about 12%.

In some particular embodiments, the amount of an organic UV filter is present in the composition in the range of from about 1% to about 15%, or from about 2% to about 10%, or from about 3% to about 9%, or at about 5%, or any suitable combination, sub-combination, range, or sub-range thereof by weight, based on the weight of the composition. In some particular embodiments, the UV filter system includes an organic UV filter comprising ethylhexyl salicylate that is present in an amount from about 1% to up to 5%. In some particular embodiments, the UV filter system includes homosalate that is present in an amount from about 3% to about 9%. The composition may include other organic UV filters and may further include SPF boosters.

Thus, any one UV filter may be present, by weight, based on the total weight of the composition, from about 1, 2, 3, 4, 5, 6, 7, 8, 9, 10, 11, 12, 13, 14, to about 15 weight percent, including increments and ranges therein and there between.

In accordance with the various embodiments, the total amount of UV filters present in the systems and compositions can range from about 15% to about 35% or from about 20% to about 30%, or from about 20% to about 25%, or any suitable combination, sub-combination, range, or sub-range thereof by weight, based on the weight of the composition. In some particular embodiments, the UV filters are present from at least about 15%, or from at least about 18%, or from at least about 20%, or from at least about 22%, or from at least about 24%, or from at least about 25%, or from at least about 28% by weight based on the weight of the composition. One of ordinary skill in the art, however, will appreciate that other ranges are within the scope of the invention.

Thus, the combination of UV filters present, by weight, based on the total weight of the composition, is from about 15, 16, 17, 18, 19, 20, 21, 22, 23, 24, 25, 26, 27, 28, 29, 30, 31, 32, 33, 34, to about 35 weight percent, including increments and ranges therein and there between.

In accordance with the disclosure, the amount of the mineral UV filters and the amount of the organic UV filters present in the system are at a weight ratio of inorganic/mineral to organic is about 12:14-17, based on the total weight of the UV filter system. Thus, the weight ratio of inorganic/mineral:organic is in the range from about 1:1 to about 1:1.5, or from about 1:1.15 to about 1:1.5. In some particular embodiments, the weight ratio of inorganic/mineral:organic UV filters is 1:1.14.

Examples of Inorganic and Organic UV Filters are Provided Herein Below

Inorganic UV Filters

In some embodiments, the composition may comprise one or more inorganic UV filter. If two or more inorganic UV filters are used, they may be the same or different.

The inorganic UV filter used for the present disclosure may be active in the UV-A and/or UV-B region. The inorganic UV filter may be hydrophilic and/or lipophilic. The inorganic UV filter is, in some embodiments, insoluble in solvents, such as water, and ethanol commonly used in cosmetics.

It is in some embodiments desirable that the inorganic UV filter be in the form of a fine particle such that the mean (primary) particle diameter thereof ranges from 1 nm to 50 nm, and in some embodiments 5 nm to 40 nm, and in some embodiments 10 nm to 30 nm. The mean (primary) particle size or mean (primary) particle diameter herein is an arithmetic mean diameter.

The inorganic UV filter can be selected from the group consisting of silicon carbide, metal oxides, which may or may not be coated, and mixtures thereof. And in some embodiments, the inorganic UV filters are selected from pigments (mean size of the primary particles: generally from 5 nm to 50 nm, and in some embodiments from 10 nm to 50 nm) formed of metal oxides, such as, for example, pigments formed of titanium oxide (amorphous or crystalline in the rutile and/or anatase form), iron oxide, zinc oxide, zirconium oxide, or cerium oxide, which are all UV photoprotective agents that are well known per se. And in some embodiments, the inorganic UV filters are selected from titanium oxide, zinc oxide, and in some embodiments, titanium oxide.

The inorganic UV filter may or may not be coated. The inorganic UV filter may have one or more coating. The coating may comprise one or more compound selected from the group consisting of alumina, silica, aluminum hydroxide, silicones, silanes, fatty acids or salts thereof (such as sodium, potassium, zinc, iron, or aluminum salts), fatty alcohols, lecithin, amino acids, polysaccharides, proteins, alkanolamines, waxes, such as beeswax, (meth)acrylic polymers, organic UV filters, and (per)fluoro compounds. It is in some embodiments desirable for the coating to include one or more organic UV filter.

Of course, the inorganic UV filter made of metal oxides may, before their treatment with silicones, have been treated with other surfacing agents, in particular, with cerium oxide, alumina, silica, aluminum compounds, silicon compounds, or their mixtures. The coated inorganic UV filter may have been prepared by subjecting the inorganic UV filter to one or more surface treatments of a chemical, electronic, mechano-chemical, and/or mechanical nature with any of the compounds as described above, as well as polyethylenes, metal alkoxides (titanium or aluminum alkoxides), metal oxides, sodium hexametaphosphate, and those shown, for example, in Cosmetics & Toiletries, February 1990, Vol. 105, pp. 53-64.

The coated inorganic UV filter may be titanium oxides coated: with silica, such as the product "Sun veil" from Ikeda, and "Sunsil TIN 50" from Sunjin Chemical; with silica and with iron oxide, such as the product "Sunveil F" from Ikeda; with silica and with alumina, such as the products "Microtitanium Dioxide MT 500 SA" from Tayca, "Tioveil" from Tioxide, and "Mirasun TiW 60" from Rhodia; with alumina, such as the products "Tipaque TTO-55 (B)" and "Tipaque TTO-55 (A)" from Ishihara, and "UVT 14/4" from Kemira; with alumina and with aluminum stearate, such as the product "Microtitanium Dioxide MT 100 T, MT 100 TX, MT 100 Z or MT-01" from Tayca, the products "Solaveil CT-10 W" and "Solaveil CT 100" from Uniqema, and the product "Eusolex T-AVO" from Merck; with alumina and with aluminum laurate, such as the product "Microtitanium Dioxide MT 100 S" from Tayca; with iron oxide and with iron stearate, such as the product "Microtitanium Dioxide MT 100 F" from Tayca; with zinc oxide and with zinc stearate, such as the product "BR351" from Tayca; with silica and with alumina and treated with a silicone, such as the products "Microtitanium Dioxide MT 600 SAS", "Microtitanium Dioxide MT 500 SAS", and "Microtitanium Dioxide MT 100 SAS" from Tayca; with silica, with alumina and with aluminum stearate and treated with a silicone, such as the product "STT-30-DS" from Titan Kogyo; with silica and treated with a silicone, such as the product "UV-Titan X 195" from Kemira; with alumina and treated with a silicone, such as the products "Tipaque TTO-55 (S)" from Ishihara or "UV Titan M 262" from Kemira; with triethanolamine, such as the product "STT-65-S" from Titan Kogyo; with stearic acid, such as the product "Tipaque TTO-55 (C)" from Ishihara; or with sodium hexametaphosphate, such as the product "Microtitanium Dioxide MT 150 W" from Tayca. Other titanium oxide pigments treated with a silicone are, and in some embodiments TiO2 treated with octyltrimethylsilane and for which the mean size of the individual particles is from 25 and 40 nm, such as that marketed under the trademark "T 805" by Degussa Silices, TiO2 treated with a polydimethylsiloxane and for which the mean size of the individual particles is 21 nm, such as that marketed under the trademark "70250 Cardre UF TiO2Si3" by Cardre, and anatase/rutile TiO2 treated with a polydimethylhydrosiloxane and for which the mean size of the individual particles is 25 nm, such as that marketed under the trademark "Microtitanium Dioxide USP Grade Hydrophobic" by Color Techniques.

And in some embodiments, the following coated TiO2 can be used as the coated inorganic UV filter: Stearic acid (and) Aluminum Hydroxide (and) TiO2, such as the product "MT-100 TV" from Tayca, with a mean primary particle diameter of 15 nm; Dimethicone (and) Stearic Acid (and) Aluminum Hydroxide (and) TiO2, such as the product "S A-TTO-54" from Miyoshi Kasei, with a mean primary particle diameter of 15 nm; Silica (and) TiO2, such as the product "MT-100 WP" from Tayca, with a mean primary particle diameter of 15 nm; Dimethicone (and) Silica (and) Aluminum Hydroxide (and) TiO2, such as the product "MT-Y02" and "MT-Y-110 M3S" from Tayca, with a mean primary particle diameter of 10 nm; Dimethicone (and) Aluminum Hydroxide (and) TiO2, such as the product "SA-TTO-S3" from Miyoshi Kasei, with a mean primary particle diameter of 15 nm; Dimethicone (and) Alumina (and) TiO2, such as the product "UV TITAN MI 70" from Sachtleben, with a mean primary particle diameter of 15 nm; and Silica (and) Aluminum Hydroxide (and) Alginic Acid (and) TiO2, such as the product "MT-100 AQ" from Tayca, with a mean primary particle diameter of 15 nm. In terms of UV filtering ability, TiO2 coated with one or more organic UV filter is more desirable. For example, Avobenzone (and) Stearic Acid (and) Aluminum Hydroxide (and) TiO2, such as the product "HXMT-100ZA" from Tayca, with a mean primary particle diameter of 15 nm, can be used.

The uncoated titanium oxide pigments are, for example, marketed by Tayca under the trademarks "Microtitanium Dioxide MT500B" or "Microtitanium Dioxide MT600B", by Degussa under the trademark "P 25", by Wacker under the trademark "Oxyde de titane transparent PW", by Miyoshi Kasei under the trademark "UFTR", by Tomen under the trademark "ITS" and by Tioxide under the trademark "Tioveil AQ". The uncoated zinc oxide pigments are, for example: those marketed under the trademark "Z-cote" by Sunsmart; those marketed under the trademark "Nanox" by Elementis; and those marketed under the trademark "Nanogard WOO 2025" by Nanophase Technologies. The coated zinc oxide pigments are, for example: those marketed under the trademark "Oxide Zinc CS-5" by Toshiba (ZnO coated with polymethylhydrosiloxane); those marketed under the trademark "Nanogard Zinc Oxide FN" by Nanophase Technologies (as a 40% dispersion in Finsolv TN; C12-C15 alkyl benzoate); those marketed under the trademark "Daitopersion Zn-30" and "Daitopersion Zn-50" by Daito (dispersions in oxyethylenated polydimethylsiloxane/cyclopolymethylsiloxane comprising 30% or 50% of zinc nano-oxides coated with silica and polymethylhydrosiloxane); those marketed under the trademark "NFD Ultrafine ZnO" by Daikin (ZnO coated with phosphate of perfluoroalkyl and a copolymer based on perfluoroalkylethyl as a dispersion in cyclopentasiloxane); those marketed under the trademark "SPD-Z1" by Shin-Etsu (ZnO coated with a silicone-grafted acrylic polymer dispersed in cyclodimethylsiloxane); those marketed under the trademark "Escalol Z100" by ISP (alumina-treated ZnO dispersed in an ethylhexyl methoxycinnamate/PVP-hexadecene copolymer/methicone mixture); those marketed under the trademark "Fuji ZnO-SMS-10" by Fuji Pigment (ZnO coated with silica and polymethylsilsesquioxane); and those marketed under the trademark "Nanox Gel TN" by Elementis (ZnO dispersed at 55% in C12-C15 alkyl benzoate with hydroxystearic acid polycondensate). The uncoated cerium oxide pigments are marketed, for example, under the trademark "Colloidal Cerium Oxide" by Rhone-Poulenc.

The uncoated iron oxide pigments are, for example; marketed by Arnaud under the trademarks "Nanogard WOO 2002 (FE 45B)", "Nanogard Iron FE 45 BL AQ", "Nanogard FE 45R AQ", and "Nanogard WCD 2006 (FE 45R)", or by Mitsubishi under the trademark "TY-220". The coated iron oxide pigments are, for example; marketed by Arnaud under the trademarks "Nanogard WCD 2008 (FE 45B FN)", "Nanogard WCD 2009 (FE 45B 556)", "Nanogard FE 45 BL 345", and "Nanogard FE 45 BL", or by BASF under the trademark "Oxyde de fer transparent".

Mention may also be made of mixtures of metal oxides, in particular, of titanium dioxide and of cerium dioxide, including a mixture of equal weights of titanium dioxide coated with silica and of cerium dioxide coated with silica marketed by Ikeda under the trademark "Sunveil A", and also a mixture of titanium dioxide and of zinc dioxide coated with alumina, with silica and with silicone, such as the product "M 261" marketed by Kemira, or coated with alumina, with silica and with glycerol, such as the product "M 211" marketed by Kemira. Coated inorganic UV filters are desirable, because the UV filtering effects of the inorganic UV filters can be enhanced. In addition, the coating(s) may help uniformly or homogeneously disperse the UV filters in the composition, according to the present disclosure.

Organic UV Filters

The compositions, according to the disclosure, may comprise one or more organic UV filter. If two or more organic UV filters are used, they may be the same or different. The organic UV filter used for the present disclosure may be active in the UV-A and/or UV-B region. The organic UV filter may be hydrophilic and/or lipophilic. The organic UV filter may be solid or liquid. The terms "solid" and "liquid" mean solid and liquid, respectively, at 25° C. under 1 atm.

The organic UV filter can be selected from the group consisting of anthranilic compounds; dibenzoylmethane compounds; cinnamic compounds; salicylic compounds; camphor compounds; benzophenone compounds; ÿ,ÿ-diphenylacrylate compounds; triazine compounds; benzotriazole compounds; benzalmalonate compounds; benzimidazole compounds; imidazoline compounds; bis-benzoazolyl compounds; p-aminobenzoic acid (PABA) compounds; methylenebis(hydroxyphenylbenzotriazole) compounds; benzoxazole compounds; screening polymers and screening silicones; dimers derived from a-alkylstyrene; 4,4-diarylbutadienes compounds; guaiazulene and derivatives thereof; rutin and derivatives thereof; flavonoids; bioflavonoids; oryzanol and derivatives thereof; quinic acid and derivatives thereof; phenols; retinol; cysteine; aromatic amino acids; peptides having an aromatic amino acid residue; and mixtures thereof.

Mention may be made, as examples of the organic UV filter(s), of those denoted below under their INCI names, and mixtures thereof. Anthranilic compounds: Menthyl anthranilate, marketed under the trademark "Neo Heliopan MA" by Haarmann and Reimer. Dibenzoylmethane compounds: Butyl methoxydibenzoylmethane, marketed, in particular, under the trademark "Parsol 1789" by Hoffmann-La Roche; and isopropyl dibenzoylmethane. Cinnamic compounds: Ethylhexyl methoxycinnamate, marketed, in particular, under the trademark "Parsol MCX" by Hoffmann-La Roche; isopropyl methoxycinnamate; isopropoxy methoxycinnamate; isoamyl methoxycinnamate, marketed under the trademark "Neo Heliopan E 1000" by Haarmann and Reimer; cinoxate (2-ethoxyethyl-4-methoxy cinnamate); DEA methoxycinnamate; diisopropyl methylcinnamate; and glyceryl ethylhexanoate dimethoxycinnamate. Salicylic compounds: Homosalate (homomentyl salicylate), marketed under the trademark "Eusolex HMS" by Rona/EM Industries; ethylhexyl salicylate, marketed under the trademark "Neo Heliopan OS" by Haarmann and Reimer; glycol salicylate; butyloctyl salicylate; phenyl salicylate; dipropyleneglycol salicylate, marketed under the trademark "Dipsal" by Scher; and TEA salicylate, marketed under the trademark "Neo Heliopan TS" by Haarmann and Reimer. Camphor compounds, in particular, benzylidenecamphor derivatives: 3-benzylidene camphor, manufactured under the trademark "Mexoryl SD" by Chimex; 4-methylbenzylidene camphor, marketed under the trademark "Eusolex 6300" by Merck; benzylidene camphor sulfonic acid, manufactured under the trademark "Mexoryl SL" by Chimex; camphor benzalkonium methosulfate, manufactured under the trademark "Mexoryl SO" by Chimex; terephthalylidene dicamphor sulfonic acid, manufactured under the trademark "Mexoryl SX" by Chimex; and polyacrylamidomethyl benzylidene camphor, manufactured under the trademark "Mexoryl SW" by Chimex. Benzophenone compounds: Benzophenone-1 (2,4-dihydroxybenzophenone), marketed under the trademark "Uvinul 400" by BASF; benzophenone-2 (Tetrahydroxybenzophenone), marketed under the trademark "Uvinul D50" by BASF; Benzophenone-3 (2-hydroxy-4-methoxybenzophenone) or oxybenzone, marketed under the trademark "Uvinul M40" by BASF; benzophenone-4 (hydroxymethoxy benzophonene sulfonic acid), marketed under the trademark "Uvinul MS40" by BASF; benzophenone-5 (Sodium hydroxymethoxy benzophenone Sulfonate); benzophenone-6 (dihydroxy dimethoxy benzophenone); marketed under the trademark "Helisorb 11" by Norquay; benzophenone-8, marketed under the trademark "Spectra-Sorb UV-24" by American Cyanamid; benzophenone-9 (Disodium dihydroxy dimethoxy benzophenonedisulfonate), marketed under the trademark "Uvinul DS-49" by BASF; and benzophenone-12, and n-hexyl 2-(4-diethylamino hydroxybenzoyl)benzoate (UVINUL A+ by BASF). ÿ,ÿ-Diphenylacrylate compounds: Octocrylene, marketed in particular under the trademark "Uvinul N539" by BASF; and Etocrylene, marketed in particular under the trademark "Uvinul N35" by BASF. Triazine compounds: Diethylhexyl butamido triazone, marketed under the trademark "Uvasorb HEB" by Sigma 3V; 2,4,6-tris(dineopentyl 4'-aminobenzalmalonate)-s-triazine, bis-ethylhexyloxyphenol methoxyphenyl triazine marketed under the trademark «TINOSORB S» by CIBA GEIGY, and ethylhexyl triazone marketed under the trademark «UVTNUL T150 » by BASF. Benzotriazole compounds, in particular, phenylbenzotriazole derivatives: 2-(2H-benzotriazole-2-yl)-6-dodecyl-4-methylpheno, branched and linear; and those described in U.S. Pat. No. 5,240,975. Benzalmalonate compounds: Dineopentyl 4'-methoxybenzalmalonate, and polyorganosiloxane comprising benzalmalonate functional groups, such as polysilicone-15, marketed under the trademark "Parsol SLX" by Hoffmann-LaRoche. Benzimidazole compounds, in particular, phenylbenzimidazole derivatives: Phenylbenzimidazole sulfonic acid, marketed in particular under the trademark "Eusolex 232" by Merck, and disodium phenyl dibenzimidazole tetrasulfonate, marketed under the trademark "Neo Heliopan AP" by Haarmann and Reimer. Imidazoline compounds: Ethylhexyl dimethoxybenzylidene dioxoimidazoline propionate. Bis-benzoazolyl compounds: The derivatives as described in EP-669,323 and U.S. Pat. No. 2,463,264. Para-aminobenzoic acid compounds: PABA (p-aminobenzoic acid), ethyl PABA, Ethyl dihydroxypropyl PABA, pentyl dimethyl PABA, ethylhexyl dimethyl PABA, marketed, in particular, under the trademark "Escalol 507" by ISP, glyceryl PABA, and PEG-25 PABA, marketed under the trademark "Uvinul P25" by BASF. Methylene bis-(hydroxyphenylbenzotriazol) compounds, such as 2,2'-methylenebis[6-(2H-benzotriazol-2-yl)-4-methyl-phenol] marketed in the solid form under the trademark "Mixxim BB/200" by Fairmount Chemical, 2,2'-methylenebis[6-(2H-benzotriazol-2-yl)-4-(1,1,3,3-tetramethylbutyl)phenol] marketed in the micronized form in aqueous dispersion under the trademark "Tinosorb M" by BASF, or under the trademark "Mixxim BB/100" by Fairmount Chemical, and the derivatives as described in U.S. Pat. Nos. 5,237,071 and 5,166,355, GB-2,303,549, DE-197,26,184, and EP-893,119, and Drometrizole trisiloxane, marketed under the trademark "Silatrizole" by Rhodia Chimie or—"Mexoryl XL" by L'Oreal. Benzoxazole compounds: 2,4-bis[5-I(dimethylpropyl)benzoxazol-2-yl-(4-phenyl)imino]-6-(2-ethylhexyl) imino-1,3,5-triazine, marketed under the trademark of Uvasorb K2A by Sigma 3V. Screening polymers and screening silicones: The silicones described in WO 93/04665. Dimers derived from a-alkylstyrene: The dimers described in DE-19855649. 4,4-Diarylbutadiene compounds: I,I-dicarboxy(2,2'-dimethylpropyl)-4,4-diphenylbutadiene.

In some embodiments the organic UV filter(s) may be selected from the group consisting of: butyl methoxydibenzoylmethane, ethylhexyl methoxycinnamate, homosalate, ethylhexyl salicylate, phenylbenzimidazole sulfonic acid, benzophenone-3, benzophenone-4, benzophenone-5, n-hexyl 2-(4-diethylamino-2-hydroxybenzoyl)benzoate, I,r-(I,4-piperazinediyl)bis[I-2-[4-(diethylamino)-2-hydroxybenzoyl]phenyl]-methanone 4-methylbenzylidene camphor, terephthalylidene dicamphor sulfonic acid, disodium phenyl dibenzimidazole tetrasulfonate, ethylhexyl triazone, bis-ethylhexyloxyphenol methoxyphenyl triazine, diethylhexyl butamido triazone, 2,4,6-tris(dineopentyl 4'-aminobenzalmalonate)-s-triazine, 2,4,6-tris(diisobutyl 4'-aminobenzalmalonate)-s-triazine, 2,4-bis-(n-butyl 4'-aminobenzalmalonate)-6-[(3-{1, 3, 3, 3-tetramethyl-1-[(trimethylsilyloxy]-disiloxanyl}propyl)amino]-s-triazine, 2,4,6-tris-(di-phenyl)-triazine, 2,4,6-tris-(ter-phenyl)-triazine, methylene bis-benzotriazolyl tetramethylbutylphenol, drometrizole trisiloxane, polysilicone-15, dineopentyl 4'-methoxybenzalmalonate, I,I-dicarboxy(2,2'-dimethylpropyl)-4,4-diphenylbutadiene, 2,4-bis[5-I (dimethylpropyl)benzoxazol-2-yl-(4-phenyl)imino]-6-(2-ethylhexyl)imino-I,3,5-triazine, camphor benzylkonium methosulfate, and mixtures thereof.

SPF Boosters

In accordance with some embodiments, the composition according to the disclosure may comprise one or more SPF booster. The term "SPF booster" means a compound or composition that, when used in a composition in conjunction with a UV screening agent, increases the SPF value of the composition without increasing the amount of the UV screening agent in the composition.

In some embodiments, the SPF booster may be selected from one or more material selected from the group consisting of (co)polymers of (meth)acrylic acid, (meth)acrylates, and/or styrene; glass; silica; and mixtures thereof. As the (co)polymers of (meth)acrylic acid, (meth)acrylates, and/or styrene, mention may be made of poly(meth)acrylates, such as PMMA, a copolymer of (meth)acrylic acid and (meth) acrylates, and a copolymer of (meth)acrylic acid, (meth) acrylates, and styrene. In some embodiments, an SPF booster may be one of a styrene/acrylates copolymer and a silicone polymer comprising dimethicone (and) dimethicone/vinyl dimethicone crosspolymer.

In some embodiments, the SPF booster is an oil soluble film former selected from ethylenediamine/stearyl dimer dilinoleate copolymer, vp/hexadecene copolymer, vp/eicosene copolymer, synthetic wax, beeswax, polyethylene, perfluoroperhydrophenanthrene, adipic acid/diethylene glycol/glycerin crosspolymer, trimethylpentanediol/adipic acid/glycerin copolymer, hydrogenated styrene/butadiene coplymer, hydrogenated styrene/isoprene copolymer, hydrogenated polycyclopentadiene, and propylsilsesquioxane wax substituted with alkyl units having at least 30 carbons.

In some embodiments, the SPF booster may be selected from silicone film formers. In some embodiments, the silicone film former may be selected from a silicone acrylate. In some particular embodiments the one or more SPF booster comprises one or more silicone film former that comprises a silicone acrylate copolymer. Some representative examples of silicone acrylates film formers include dimethicone (and) dimethiconol, dimethicone (and) acrylates/dimethicone copolymer, and acrylates/polytrimethylsiloxymethacrylate copolymer. In some embodiments, a silicone film former is selected from one or a combination of dimethicone (and) dimethiconol, and dimethicone (and) acrylates/dimethicone copolymer.

In some embodiments, the SPF booster is selected from one or more of Ethylenediamine/Stearyl Dimer Dilinoleate Copolymer, Butyloctyl Salicylate, and Dimethicone and Acrylates/Dimethicone Copolymer, a styrene/acrylates copolymer, a silicone polymer comprising dimethicone (and) dimethicone/vinyl dimethicone crosspolymer, sunspheres, one or more of film formers oleocraft and KP545-L, and the UVA booster Solastay.

SPF boosters may be present in the composition according to the invention, at a concentration, from about 0.01% to 25%, in some embodiments from about 0.1% to 13%, and in some embodiments from about 0.5% to 10% by weight, all weights based on the total weight of the composition. Thus, in various embodiments, an SPF booster, when present, may be present in a composition in a weight percent amount from 0.01, 0.02, 0.03, 0.04, 0.05, 0.06, 0.07, 0.08, 0.09, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 24.0 to 25.0 percent by weight, including increments there between.

In some particular embodiments comprising an SPF booster that is a silicone film former, the SPF booster may be present from about 0.1% to about 5.0%, or from about 0.3% to about 3.0%, or from about 0.4% to about 4%, or from about 0.5% to about 2.5%, or any suitable combination, sub-combination, range, or sub-range thereof by weight, based on the weight of the composition. One of ordinary skill in the art, however, will appreciate that other ranges are within the scope of the invention.

Thus, the one or combination of silicone film formers, when in the composition, may be present by weight, based on the total weight of the composition, from about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5 to about 5.0 percent, including increments and ranges therein and there between.

Emulsifier (Surfactant) System

The emulsifier (or surfactant) system is comprised of one or more anionic surfactant, one or more nonionic surfactant having an HLB of greater than or equal to about 14, and one or more nonionic surfactant having an HLB of less than or equal to about 10.

In accordance with the disclosure, the emulsifier system is present in the composition in the range from about 1% to about 15% based on the total weight of the composition. In accordance with the various embodiments, the amount of each emulsifier present in the compositions can range from about 0.1% to about 10%, or from about 0.2% to about 7%, or from about 0.5% to about 5% or any suitable combination, sub-combination, range, or sub-range thereof by weight, based on the weight of the composition. One of ordinary skill in the art, however, will appreciate that other ranges are within the scope of the invention.

In some particular embodiments, the amount of an emulsifier is present in the composition in the range of from about 0.1% to about 15%, or from about 0.3% to about 8%, or from about 0.4% to about 2% or at about 0.45, or any suitable combination, sub-combination, range, or sub-range thereof by weight, based on the weight of the composition. In some particular embodiments, the emulsifier system includes an anionic emulsifier comprising potassium cetyl phosphate present in an amount that is about 0.5%. In some particular embodiments, the emulsifier system includes a nonionic high HLB emulsifier comprising PEG-40 stearate present in an amount that is about 1.5% and a combination of low HLB emulsifiers comprising polysorbate 61 present in an amount that is about 1.75% and sorbitan tristearate present in an amount that is about 1.25%.

Thus, any one emulsifier present, by weight, based on the total weight of the composition, from about 0.1, 0.2, 0.3, 0.4, 0.5, 0.6, 0.7, 0.8, 0.9, 1, 2, 3, 4, 5, 6, 7, 8, 9, 10, 11, 12, 13, 14, to about 15 weight percent, including increments and ranges therein and there between.

Emulsifiers/Surfactants

As used herein the term "anionic surfactant" means a surfactant comprising, as ionic or ionizable groups, only anionic groups. These anionic groups are preferably chosen from the groups $CO_2H$, $CO_2^-$, $SO_3H$, $SO_3^-$, $OSO_3H$, $OSO_3^-$, $H_2PO_3$, $HPO_3^-$, $PO_3^{2-}$, $H_2PO_2^-$, $HPO_2^-$, $PO_2^{2-}$, POH and PO.

In various embodiments, anionic surfactants which can be used in the composition according to the invention may be selected from alkyl sulfates, alkyl ether sulfates, alkylamido ether sulfates, alkylaryl polyether sulfates, monoglyceride sulfates, alkylsulfonates, alkylamidesulfonates, alkylarylsulfonates, a-olefmsulfonates, paraffin sulfonates, alkyl sulfo succinates, alkyl ether sulfosuccinates, alkylamide sulfosuccinates, alkyl sulfoacetates, acyl sarcosinates, acyl glutamates, alkyl sulfosuccinamates, acyl isethionates and N-acyltaurates, salts of alkyl monoesters of polyglycoside-polycarboxylic acids, acyl lactylates, D-galactoside-uronic acid salts, alkyl ether carboxylic acid salts, alkylaryl ether carboxylic acid salts, alkylamido ether carboxylic acid salts; and the corresponding non-salified forms of all these compounds; the alkyl and acyl groups of all these compounds comprising from 6 to 40 carbon atoms and preferably from 6 to 24 carbon atoms and the aryl group denoting a phenyl group.

In various embodiments, anionic surfactants include anionic amphiphilic lipids which can be chosen from: 1) mixed esters of fatty acid or of fatty alcohol, of carboxylic acid and of glycerol, 2) alkyl ether citrates, 3) alkenyl succinates chosen from alkoxylated alkenyl succinates, alkoxylated glucose alkenyl succinates and alkoxylated methylglucose alkenyl succinates, and 4) phosphoric acid fatty esters.

Examples of the mixed esters of fatty acid or of fatty alcohol, of carboxylic acid and of glycerol which can be used as anionic amphiphilic lipids in the composition, according to the invention, can be chosen in particular from the group including mixed esters of fatty acid or of fatty alcohol having an alkyl chain including from 8 to 22 carbon atoms and of α-hydroxy acid and/or of succinic acid with glycerol. The α-hydroxy acid can be, for example, citric acid, lactic acid, glycolic acid, malic acid and their mixtures.

Examples of the alkyl chain of the fatty acids or alcohols from which the mixed esters which can be used as anionic surfactants in the composition of the invention derive can be saturated or unsaturated and linear or branched. It can, in particular, be stearate, isostearate, linoleate, oleate, behenate, arachidonate, palmitate, myristate, laurate, caprate, isostearyl, stearyl, linoleyl, oleyl, behenyl, myristyl, lauryl and capryl chains and their mixtures.

Mention may be made, as examples of mixed esters which can be used in the composition of the invention, of the mixed ester of glycerol and of the mixture of citric, lactic, linoleic and oleic acids (INCI name: Glyceryl citrate/lactate/linoleate/oleate) sold by Hills under the name Imwitor 375; the mixed ester of succinic acid and of isostearyl alcohol with glycerol (INCI name: Isostearyl diglyceryl succinate) sold by Huls under the name Imwitor 780 K; the mixed ester of citric acid and of stearic acid with glycerol (INCI name: Glyceryl stearate citrate) sold by Hills under the name Imwitor 370; or the mixed ester of lactic acid and of stearic acid with glycerol (INCI name: Glyceryl stearate lactate) sold by Danisco under the name Lactodan B30 or Rylo LA30.

Examples of the alkyl ether citrates, which can be used as anionic surfactants in the composition, according to the invention, can be chosen in particular from the group including the monoesters, diesters or triesters formed by citric acid and at least one oxyethylenated fatty alcohol, including a saturated or unsaturated and linear or branched alkyl chain having from 8 to 22 carbon atoms and including from 3 to 9 ethoxylated groups, and their mixtures. This is because it is possible to use a mixture of one or more of these citrates in the composition of the invention.

These citrates can be chosen, for example, from the mono-, di- and triesters of citric acid and of ethoxylated lauryl alcohol, including from 3 to 9 ethoxylated groups, sold by Witco under the name Witconol EC, in particular Witconol EC 2129, which is predominantly a dilaureth-9 citrate, and Witconol EC 3129, which is predominantly a trilaureth-9 citrate.

The alkyl ether citrates used as anionic surfactants lipids are preferably employed in the form neutralized to a pH of approximately 7, the neutralizing agent being chosen from inorganic bases, such as sodium hydroxide, potassium hydroxide or ammonia, and organic bases, such as mono-, di- and triethanolamine, aminomethylpropane-1,3-diol, N-methylglucamine or basic amino acids, such as arginine and lysine, and their mixtures.

The alkenyl succinates which can be used as anionic surfactants in the composition of the invention are in particular, ethoxylated and/or propoxylated derivatives and they are preferably chosen from the compounds of one of the following formulae (I) or (II)

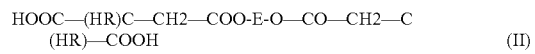

in which: the R and R' radicals are chosen from linear or branched alkyl radicals including from 6 to 22 carbon atoms (which range expressly includes 10, 12, 14, 16, 18, and 20), E is chosen from oxyethylene chains of formula (C2H4O)n in which n ranges from 2 to 100 (which range expressly includes 10, 20, 40, 60, 80 and 90), oxypropylene chains of formula (C3H6O)n', in which n' ranges from 2 to 100 (which range expressly includes 5, 10, 20, 30, 40, 50, 60, 70, 80 and 90), random or blocked copolymers including 5 oxyethylene chains of formula (C2H4O)n and oxypropylene chains of formula (C3H6O)n' such that the sum of n and n' ranges from 2 to 100 (which range expressly includes 5, 10, 20, 30, 40, 50, 60, 70, 80 and 90), oxyethylenated and/or oxypropylenated glucose groups including, on average, from 4 to 100 oxyethylene and/or oxypropylene units distributed over all the hydroxyl functional groups, or oxyethylenated and/or oxypropylenated methylglucose groups including, on average, from 4 to 100 oxyethylene and/or oxypropylene units distributed over all the hydroxyl functional groups (which ranges expressly include 5, 10, 20, 30, 40, 50, 60, 70, 80 and 90).

In the formulae (I) and (II), n and n' are mean values and are therefore not necessarily integers. The choice is advantageously made, for n, of a value ranging from 5 to 60 and more preferably still from 10 to 30.

The R and/or R' radical is advantageously chosen from linear alkyl radicals including from 8 to 22 and preferably from 14 to 22 carbon atoms (which ranges expressly include 10, 12, 14, 16, 18 and 20 carbons as appropriate). Preferably, it can be, for example, the hexadecenyl radical, including 16 carbon atoms, or the octadecenyl radical, including 18 carbon atoms.

The compounds of formulae (I) and (II) described above in which E is chosen from oxyethylene chains, oxypropylene chains and copolymers including oxyethylene chains and oxypropylene chains can be prepared in accordance with the description which is given in documents WO-A-94/00508, EP-A-1 071 99 and GB-A-2 131 820, the entire contents of each of which are incorporated herein by reference.

The acid functional group —COOH of the anionic surfactants of formulae (I) and (II) is generally found in the composition of the invention in the form neutralized by a neutralizing agent, the neutralizing agent being chosen, for example, from inorganic bases, such as sodium hydroxide, potassium hydroxide or ammonia, and organic bases, such as mono-, di- and triethanolamine, aminomethylpropane-1, 3-diol, N-methylglucamine or basic amino acids, such as arginine and lysine, and their mixtures.

Examples of the phosphoric acid fatty esters and their oxyethylenated derivatives, which can be used as anionic surfactants in the compositions, according to the invention, can be chosen in particular from the group including the esters formed of phosphoric acid and of at least one alcohol including a saturated or unsaturated and linear or branched alkyl chain having from 8 to 22 carbon atoms (which range expressly includes 10, 12, 14, 16, 18 and 20) and the esters formed of phosphoric acid and of at least one ethoxylated alcohol including a saturated or unsaturated and linear or branched alkyl chain having from 8 to 22 carbon atoms (which range expressly includes 10, 12, 14, 16, 18 and 20) and including from 2 to 40 oxyethylene groups (which range expressly includes 4, 6, 8, 10, 12, 14, 16, 18, 20 and 30), their salts and their mixtures. This is because it is possible to use a mixture of one or more of these phosphoric acid esters in the composition of the invention.

These esters can be chosen in particular from esters of phosphoric acid and of C9-C15 alcohols or their salts, such as the potassium salt of C9-C15 alkyl phosphate sold under the name Arlatone MAP by ICI; esters of phosphoric acid and of stearyl and/or isostearyl alcohols, such as the phosphate of stearyl/isostearyl alcohols (INCI name: Octyldecyl phosphate) sold under the name Hostaphat CG120 by Hoechst Celanese; esters of phosphoric acid and of cetyl alcohol, and their oxyethylenated derivatives, such as the product sold under the name Crodafos CES (mixture of cetearyl alcohol, of dicetyl phosphate and of ceteth-10 phosphate) by Croda, or esters of phosphoric acid and of tridecyl alcohol, and their oxyethylenated derivatives, such as the product sold under the name Crodafos T10 (INCI name: Trideceth-10 phosphate) by Croda. The oxyethylenated derivatives of phosphoric acid and of fatty alcohol can be prepared in accordance with the description given in Patent Application WO-A-96/14145, the entire contents of which is incorporated in the present application by reference.

In some particular embodiments, the one or more anionic surfactant comprises at least potassium cetyl phosphate, which has an HLB of 9.6.

Nonionic Surfactants with Low and High HLB

Suitable nonionic surfactants having an HLB greater than or equal to about 14 include, but are not limited to, PEG-40 stearate, which has a HLB of about 17.3, Polysorbate 20, which has a HLB of about 16.7, Polysorbate 60, which has a HLB of about 14.9, Polysorbate 60 NF, which has a HLB of about 14.9, Polysorbate 80, which has a HLB of about 15, and Polysorbate 80 NF which has a HLB of about 15, and mixtures thereof. Other suitable examples having an HLB of 13 or greater are alkyl esters, ether oxyethylene (Brij and Myrj series), sucrose alkyl esters, and combinations thereof.

Suitable nonionic surfactants having an HLB of less than or equal to about 10 include, but are not limited to polysorbate 61, which has a HLB of about 9.6, sorbitan tristearate, which has a HLB of about 2.1, polyglycerides, polysorbate 65, polysorbate 81, polysorbate 85, sucrose distearate, polyglyceryl-4 isostearate (and) cetyl PEG/PPG 10/1 dimethicone (and) hexyl laurate, sorbitan stearate, octyldodecyl xyloside, glyceryl stearate, and combinations thereof.

Solvent System

In accordance with various embodiments, the composition according to the disclosure includes a solvent system that comprises one or more oils/emollients and silicones in the oily phase and water in the aqueous phase. In some embodiments, as may be exemplified here, the composition may include other solvents, in particular selected from water and alcohols.

In accordance with the disclosure, a solvent system is present in the composition in the range from about 40% to about 60% based on the total weight of the composition. In accordance with the various embodiments, the amount of each solvent present in the compositions can range from about 0.1% to about 60% based on the weight of the composition. In some embodiments, the solvent system includes water present up to about 60%, or from about 40% to about 50%. In some embodiments, the solvent system includes one or a combination of oils/emollients that can include silicone and non-silicone compounds, each of which can be present in a range from about 0.05% to about 25%, and in combination up to about 60%. In the various embodiments, the solvent system includes components present from about 0.05% to about 60%, or from about 0.05% to about 50%, or from about 0.1% to about 45%, or from about 1% to about 20%, or from about 1% to about 10%, or from about 1% to about 5% or any suitable combination, sub-combination, range, or sub-range thereof by weight, based on the weight of the composition. One of ordinary skill in the art, however, will appreciate that other ranges are within the scope of the invention.

In some particular embodiments, the solvent system includes water present in an amount that is about 45%. In some particular embodiments, the compositions include in the solvent system fatty compounds including dicaprylyl ether present in an amount that is about 1%, diisopropyl sebacate present in an amount that is about 1%, and dicaprylyl carbonate present in an amount that is about 1.5%. In some particular embodiments, the compositions include in the solvent system silicones including PEG-12 dimethicone present in an amount that is about 0.1%, dimethicone present in an amount that is about 4%, caprylyl methicone present in an amount that is about 2.5%, and, when present, dimethicone (and) acrylates/dimethicone copolymer present in an amount that is about 0.5%.

Thus, any one solvent may be present, by weight, based on the total weight of the composition, is from about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55 to about 60 weight percent, including increments and ranges therein and there between.

In accordance with various embodiments; the composition according to the disclosure includes in the solvent system one or more oils, emollients or silicones selected from: hydrocarbon-based oils of plant origin, such as liquid triglycerides of fatty acids containing from 4 to 10 carbon atoms, for instance heptanoic or octanoic acid triglycerides, or alternatively, for example, sunflower oil; corn oil, soybean oil, marrow oil, grapeseed oil, sesame seed oil, hazelnut oil, apricot oil, macadamia oil, arara oil, coriander oil, castor oil, avocado oil, caprylic/capric acid triglycerides, for instance those sold by the company Stearineries Dubois or those sold under the names Miglyol® 810, 812 and 818 by the company Dynamit Nobel, jojoba oil, shea butter oil and caprylyl glycol; synthetic esters and ethers, especially of fatty acids, for instance purcellin oil; 2-octyldodecyl stearate, 2-octyldodecyl erucate, isostearyl isostearate; hydroxylated esters, for instance isostearyl lactate, octyl hydroxystearate, octyldodecyl hydroxystearate, diisostearyl malate or triisocetyl citrate; fatty alcohol heptanoates, octanoates or decanoates; polyol esters, for instance propylene glycol dioctanoate, neopentyl glycol diheptanoate and diethylene glycol diisononanoate; and pentaerythritol esters, for instance pentaerythrityl tetraisostearate, or isopropyl lauroyl sarcosinate, sold especially under the trade name Eldew® SL 205 by the company Ajinomoto; linear or branched hydrocarbons, of mineral or synthetic origin, such as volatile or non-volatile liquid paraffins, and derivatives thereof, petroleum jelly, polydecenes, isohexadecane, isododecane, hydrogenated polyisobutene such as Parleam® oil; or the mixture of n-undecane (C11) and of n-tridecane (C13) sold under the reference Cetiol® UT by the company Cognis; fluoro oils that are partially hydrocarbon-based and/or silicone-based, for instance those described in document JP-A-2 295 912; silicone oils, for instance volatile or non-volatile polymethylsiloxanes (PDMS) with a linear or cyclic silicone chain, which are liquid or pasty at room temperature, in particular volatile silicone oils, especially cyclopolydimethylsiloxanes (cyclomethicones) such as cyclohexadimethylsiloxane and cyclopentadimethylsiloxane; polydimethylsiloxanes comprising alkyl; alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes or 2-phenylethyl trimethylsiloxy silicates, and polymethylphenylsiloxanes; mixtures thereof. Additional examples include benzoic acid esters of C9-015 alcohols, isononyl iso-nonanoate, 012-015 alkyl benzoate, or any combinations thereof.

Specific examples of oils/emollients include cocoglyceride, cyclomethicone, dimethicone, dicapryl maleate, caprylic/capric triglyceride, isopropyl myristate, octyl stearate, isostearyl linoleate, lanolin oil, coconut oil, cocoa butter, olive oil, avocado oil, aloe extracts, jojoba oil, castor oil, fatty acid, oleic acid, stearic acid, fatty alcohol, cetyl alcohol, hexadecyl alcohol, diisopropyl adipate, hydroxybenzoate esters, benzoic acid esters of C9-C15 alcohols, isononyl iso-nonanoate, alkanes, mineral oil, silicone, dimethyl polysiloxane, ether, polyoxypropylene butyl ether, polyoxypropylene cetyl ether, C12-C15 alkyl benzoate, aryl alkyl benzoate, Isopropyl Lauroyl sarcosinate, and any combinations thereof.

Examples of hydrophilic organic solvents that may be included in the sunscreen compositions include: monohydric C1-08 alcohols such as ethanol, propanol, butanol, isopropanol, isobutanol; polyethylene glycols from 6 to 80 ethylene oxides such as propylene glycol, isoprene glycol, butylene glycol, glycerol, sorbitol; mono or di-alkyl isosorbides such as dimethyl isosorbide. Examples of amphiphilic organic solvents include polypropylene glycol (PPG) like propylene glycol alkyl ester or alkyl ether of PPG like PPG-23 oleyl ether and PPG-36 oleate. The above lists are only examples and not limiting.

In some embodiments, the compositions include in the solvent system fatty compounds that are selected from one or more of dicaprylyl ether, diisopropyl sebacate, dicaprylyl carbonate. In some embodiments, the compositions include in the solvent system silicones selected from one or more of PEG-12 dimethicone, dimethicone, caprylyl methicone, and dimethicone (and) acrylates/dimethicone copolymer. In some embodiments, the compositions include in the solvent system each of dicaprylyl ether, diisopropyl sebacate, dicaprylyl carbonate, PEG-12 dimethicone, dimethicone, caprylyl methicone, and dimethicone (and) acrylates/dimethicone copolymer.

Hydrating Agents

In accordance with the disclosure, in some embodiments, one or more hydrating agents or humectants may be present in the composition. The hydrating agent present in the cosmetic composition, according to the disclosure, includes, but is not limited to, one or more of polyols, including, for example, glycerin, glycerol, glycols, such as caprylyl glycol, butylene glycol, propylene glycol, isoprene glycol, dipropylene glycol, hexylene glycol and polyethylene glycols, monoethylene glycol, diethylene glycol, triethylene glycol, diethylene glycol, hexylene glycol, glycol ethers such as monopropylene, dipropylene and tripropylene glycol alkyl (C1-C4)ethers, squalane, triacetin, sugars, such as glucose, xylitol, maltitol, sorbitol, sucrose pentaerythritol, inositol, pyrrolidone carboxylic acid, lactic acid, lithium chloride, acetamide MEA, sodium lactate, urea, dicyanamide, hyaluronic acid, aloe vera, honey, and seaweed extract.

In some embodiments, the composition includes a hydrating agent selected from one or a combination of glycerin present at about 4% and caprylyl glycol present at about 1%.

In accordance with the various embodiments, the amount of hydrating agent present in the composition can range from about 1% to about 25%, or from about 2% to about 20%, or from about 3% to about 5% or any suitable combination, sub-combination, range, or sub-range thereof by weight, based on the weight of the composition. One of ordinary skill in the art, however, will appreciate that other ranges are within the scope of the invention.

Thus, any one of or a combination of hydrating agent may be present, by weight, based on the total weight of the composition, is from about 1, 2, 3, 4, 5, 6, 7, 8, 9, 10, 11, 12, 13, 14, 15, 16, 17, 18, 19, 20, 21, 22, 23, 24, to about 25 weight percent, including increments and ranges therein and there between.

Optional Additives

The compositions can also comprise one or more additive used in the cosmetics field which does not affect the properties of the compositions according to the invention, such as fragrances, pearlescent agents, silica, preservatives, proteins, protein hydrolysates, vitamins, panthenol, silicones, odor absorbers and coloring materials; anti-microbial components, including, but not limited to, phenoxyethanol, chlorphenesin, capryloyl glycol and sodium salicylate; thickeners and fillers, for example but not limited to isohexadecane (and) disteardimonium hectorite (and) propylene carbonate, and styrene/acrylates copolymer; essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang; fruit extracts, for example Pyrus Malus (Apple) Fruit Extract, and Aloe Barbadensis Leaf Juice Powder; citric acid, sodium chloride; neutralizing or pH-adjusting agents (e.g., triethylamine (TEA) and sodium hydroxide), and combinations thereof.

Although the optional active additives are given as examples, it will be appreciated that other optional components compatible with cosmetic applications known in the art may be used. In some particular embodiments, the composition may include antimicrobials comprising one or more of chlorphenesin and phenoxyethanol. In some particular embodiments, the composition may include actives comprising one or more of tocopherol and panthenol.

In accordance with the various embodiments, the amount of each one or more actives and additives, when present in the composition can be present in a range from about 0.001% to about 20%, by weight, or from about 0.005% to about 0.01%, or from about 0.01% to about 0.1%, or from about 0.15% to about 5%, or from about 0.40% to about 4%, or from about 0.5% to about 2.5% by weight, or from about 1% to about 2%, or any suitable combination, sub-combination, range, or sub-range thereof by weight, based on the total weight of the composition. And in some embodiments, a combination of actives and additives present in the composition can be present in a range from about 0.001% to about 20%.

Thus, any one or a combination of actives and additives, when present, may be present, by weight, based on the total weight of the composition, each one or the combination present from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 weight percent, including increments and ranges therein and there between.

In some particular embodiments, additives selected from thickeners that include isohexadecane (and) disteardimonium hectorite (and) propylene carbonate, and styrene/acrylates copolymer are present in a range from about 2% to about 2% each. In some particular embodiments, additives selected from anti-microbial components that include phenoxyethanol present at about 1%, chlorphenesin present at about 0.2%, and capryloyl glycol present at about 1%, all by weight based on the weight of the composition.

EXAMPLES

Example 1: Raw Materials

The raw materials as used in the inventive compositions are set forth in Table 1, below.

TABLE 1

| Raw Materials | |
|---|---|
| INGREDIENT | SOURCE |
| ZINC OXIDE (and) TRIETHOXYCAPRYLYLSILANE | |
| POLYSORBATE 61 | CRODA |
| PEG-40 STEARATE | CRODA |
| SORBITAN TRISTEARATE | CRODA |
| POTASSIUM CETYL PHOSPHATE | DSM NUTRITIONAL PRODUCTS |
| STYRENE/ACRYLATES COPOLYMER | ROHM AND HAAS (DOW CHEMICAL) |

Example 2: Inventive Compositions

The inventive compositions as set forth in Table 2, below, include

TABLE 2

| Inventive Compositions | | | | |
|---|---|---|---|---|
| Phase | INCI US | INV 1 | INV 2 | INV 3 |
| | ACTIVES | ~1 | ~1 | ~2 |
| | ANTIMICROBIALS | 1.2 | 1.2 | 1.2 |
| | BUTYLOCTYL SALICYLATE | 3 | | 3 |
| | CAPRYLYL METHICONE | 2.5 | 2.5 | 2.5 |
| oil | DICAPRYLYL CARBONATE | 1.5 | 1.5 | 1.5 |
| oil | DICAPRYLYL ETHER | 1 | 1 | 1 |
| oil | DIISOPROPYL SEBACATE | 1 | 1 | 1 |
| oil | DIMETHICONE | 4 | 4 | 4 |
| | DIMETHICONE (and) ACRYLATES/DIMETHICONE COPOLYMER | | | 0.5 |
| | DISODIUM EDTA | 0.1 | 0.1 | 0.1 |
| | ETHYLENEDIAMINE/STEARYL DIMER DILINOLEATE COPOLYMER | 1 | 1 | 1 |
| oil | ETHYLHEXYL SALICYLATE | 5 | 5 | 5 |
| oil | HOMOSALATE | 9 | 12 | 9 |
| | HYDRATING AGENTS | 8 | 8 | 8 |
| | ISOHEXADECANE (and) DISTEARDIMONIUM HECTORITE (and) PROPYLENE CARBONATE | 2 | 2 | 2 |
| | ACTIVES | 0.6 | 0.6 | 0.6 |
| oil | PEG-12 DIMETHICONE | 0.1 | 0.1 | 0.1 |
| | PEG-40 STEARATE | 1.5 | 1.5 | 1.5 |
| | PHENOXYETHANOL | 0.98 | 0.98 | 0.98 |
| | POLYSORBATE 61 | 1.75 | 1.75 | 1.75 |
| | POTASSIUM CETYL PHOSPHATE | 0.5 | 0.5 | 0.5 |
| | SODIUM HYALURONATE | 0.1 | 0.1 | 0.1 |
| | SODIUM PCA | 0.5 | 0.5 | 0.5 |
| | SORBITAN TRISTEARATE | 1.25 | 1.25 | 1.25 |
| | STYRENE/ACRYLATES COPOLYMER | 3 | 3 | 3 |
| | WATER | 43.1 | 43.1 | 42.2 |
| | ZINC OXIDE (and) TRIETHOXYCAPRYLYLSILANE | 12.32 | 12.32 | 12.32 |
| | SPF | 40 | 40 | 40 |

Example 3: Comparative Compositions

Comparative Sunscreen compositions formulated for spray application were employed to evaluate efficacy of the inventive compositions. The comparatives included the following: Comparative 1 (COMP 1) CeraVe™ SPF 50 Spray Hybrid™ Comparative 2 (COMP 2) SkinCeuticals™ Hydrating UV Mist™; Comparative 3 (COMP 3) SkinCeuticals™ Hydrating UV Mist™; Comparative 4 (COMP 4) SkinCeuticals™ Hydrating UV Mist™ and, Comparative 5 (COMP 5) SkinCeuticals™ Hydrating UV Mist™

TABLE 4

| Comparative Compositions | | | | | |
|---|---|---|---|---|---|
| INCI (US/UE) | COMP 1 | COMP 2 | COMP 3 | COMP 4 | COMP 5 |
| BUTYLOCTYL SALICYLATE | | 3.00 | 3.00 | 3.00 | 3.00 |
| CAPRYLYL GLYCOL | 4.0 | 4.0 | 4.0 | 4.0 | 4.0 |
| CAPRYLYL METHICONE | 2.50 | 3.00 | 3.00 | 3.00 | 3.00 |

TABLE 4-continued

Comparative Compositions

| INCI (US/UE) | COMP 1 | COMP 2 | COMP 3 | COMP 4 | COMP 5 |
|---|---|---|---|---|---|
| DICAPRYLYL CARBONATE | 1.50 | 2.0 | 20.0 | 2.0 | 2.0 |
| DICAPRYLYL ETHER | 1.0 | 1.5 | 1.5 | 1.5 | 1.5 |
| DIISOPROPYL SEBACATE | 1.00 | 1.50 | 1.50 | 1.50 | 1.50 |
| DIMETHICONE | 4.00 | 6.00 | 6.00 | 6.00 | 6.00 |
| DISODIUM EDTA | 0.10 | 0.10 | 0.10 | 0.1 | 0.10 |
| DISTEARDIMONIUM HECTORITE | 0.20 | 0.20 | 0.20 | 0.20 | 0.20 |
| ETHYLENEDIAMINE/STEARYL DIMER DILINOLEATE COPOLYMER | 1 | 0.1 | 1 | 1 | 1 |
| ETHYLHEXYL SALICYLATE | 5.00 | | | 5.00 | |
| HOMOSALATE | 12.00 | | | 15.00 | |
| ISOHEXADECANE | 1.74 | 1.74 | 1.74 | 1.74 | 1.74 |
| OCTOCRYLENE | 7.00 | | | | |
| PEG-12 DIMETHICONE | 0.10 | 0.10 | 0.10 | 0.10 | 0.10 |
| PEG-40 STEARATE | 1.50 | 1.50 | 1.50 | 1.50 | 1.50 |
| PEG-8 LAURATE | 0.33 | | | 0.330 | 0.33 |
| PENTAERYTHRITYL TETRA-DI-T-BUTYL HYDROXYHYDROCINNAMATE | 0.003 | 0.003 | 0.003 | 0.003 | 0.003 |
| ANTIMICROBIALS | 1.1 | 1.1 | 1.1 | 1.1 | 1.1 |
| POLYSORBATE 61 | 1.75 | 1.75 | 1.75 | 1.75 | 1.75 |
| POTASSIUM CETYL PHOSPHATE | 0.50 | 0.50 | 0.50 | 0.50 | 0.50 |
| PROPYLENE CARBONATE | 0.06 | 0.06 | 0.06 | 0.06 | 0.06 |
| SODIUM DODECYLBENZENESULFONATE | 0.03 | | | 0.03 | 0.03 |
| SODIUM HYALURONATE | 0.10 | 0.10 | 0.10 | 0.10 | 0.10 |
| SODIUM PCA | 0.25 | 0.25 | 0.25 | 0.25 | 0.25 |
| SORBITAN TRISTEARATE | 1.25 | 1.25 | 1.25 | 1.25 | 1.25 |
| STYRENE/ACRYLATES COPOLYMER | 2.58 | | | 2.58 | 2.58 |
| ACTIVES | 0.7 | 0.65 | 0.65 | 0.65 | 0.65 |
| TRIETHOXYCAPRYLYLSILANE | 0.31 | 0.31 | 0.56 | 0.31 | 0.31 |
| WATER/AQUA | QS | QS | QS | QS | QS |
| ZINC OXIDE | 12.01200 | 12.01200 | 22.00575 | 12.01200 | 12.01200 |

Example 4: Evaluation of Compositions for Sprayability and SPF

TABLE 5

Sprayability and SPF Testing of Comparative and Inventive Compositions

| Test Composition | Characteristic | Results/Problem |
|---|---|---|
| INV 1, INV 3 | 12% ZnO, organic filters homosalate, octisalate, and booster Butyloctyl Salicylate | SPF 40; desirable galenic and sprayable |
| INV 2 | 12% ZnO, organic fillers homosalate (high), octisalate, no booster | SPF 40; desirable galenic and sprayable |
| COMP 3 | 22% ZnO (no organic filters) | Thick - would not spray |
| COMP 2, COMP 5 | 12% ZnO (no organic filters) | SPF too low |
| COMP 1 | 12% ZnO + Octocrylene | Undesirable "jet" spray pattern |
| COMP 4 | Larger oil phase (water:oil ratio of 1:>1) | Undesirable galenic |

While the disclosure has been described with reference to a preferred embodiment, it will be understood by those skilled in the art that various changes may be made, and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure is not limited to the particular embodiment disclosed as the best mode contemplated for carrying out this disclosure, but that the disclosure will include all embodiments falling within the scope of the appended claims.

The articles "a" and "an," as used herein, mean one or more when applied to any feature in embodiments of the present disclosure described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one" or "one or more" as used herein, means that there may be one, two, three or more and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed disclosure. All materials and methods described herein that embody the present disclosure can, in alternate embodiments, be more specifically defined by any of the transitional terms "comprising," "consisting essentially of," and "consisting of."

The terms "free" and "devoid" indicates that no reliably measurable excluded material is present in the composition, typically 0% by weight, based on the total weight of the composition. The term "essentially free" means that, while it prefers that no excluded material is present in the composition, it is possible to have very small amounts of the excluded material in the composition of the invention, provided that these amounts do not materially affect the advantageous properties of the composition. In particular, "essentially free" means that excluded material can be present in the composition at an amount of less than about 0.1% by weight, based on the total weight of the composition.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%— 11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. A sunscreen composition, comprising:
   a metastable oil-in-water emulsion comprising aqueous and oil phases, the composition comprising:
   a) a UV filter system comprising at least one mineral UV filter and at least one organic UV filter;
   b) an emulsification system comprising:
      at least one ionic surfactant;
      at least one surfactant having a high HLB of greater than 9;
      at least one surfactant having a low HLB of 6 or less; and
      at least one anionic emulsifier; and
   c) a solvent system comprising one or a combination of emollients and silicones, wherein the UV filter system has a weight ratio of the at least one mineral UV filter to the at least one organic UV filter of about 1:1 to about 1:1.5, and
   wherein the at least one surfactant having the high HLB includes PEG-40 stearate and polysorbate 61, the at least one surfactant having the low HLB includes sorbitan tristearate, and the emulsification system includes a ratio of the PEG-40 stearate and the polysorbate 61 to the sorbitan tristearate of about 2.6.

2. The sunscreen composition according to claim 1, wherein the components of the aqueous phase and components of the oil phase, respectively, are present in the composition at a weight ratio of aqueous components to oil components in a range from about >1:1.

3. The sunscreen composition according to claim 1, wherein a phase ratio of the aqueous phase to the non-aqueous phase is calculated based on the weight of water to the weight of non-aqueous components that include one or more of oils, esters and dimethicone present in the composition, wherein the phase ratio of the water and oil/ester/dimethicone components is from about 1.0 to about 2.0.

4. The sunscreen composition according to claim 3, wherein the phase ratio of the water and oil/ester/dimethicone components is from about 1.4 to 1.6.

5. The composition according to claim 1, wherein the weight ratio of the at least one mineral UV filter to the at least one organic UV filter is about 1:1.15 to about 1:1.5.

6. The sunscreen composition according to claim 5, wherein the weight ratio of the at least one mineral UV filter to the at least one organic UV filter is 12:14-17.

7. The sunscreen composition according to claim 1, wherein the UV filter system is present in the composition in the range from about 15% to about 35% based on the total weight of the composition.

8. The sunscreen composition according to claim 1, wherein the at least one mineral UV filter includes about 8% to about 17% by weight zinc oxide based on the total weight of the composition, and the at least one organic UV filter includes about 9% to about 12% by weight homosalate and about 0.001% to about 5% by weight octisalate based on the total weight of the composition.

9. The sunscreen composition according to claim 8, wherein the at least one mineral UV filter includes about 12% by weight of the zinc oxide based on the total weight of the composition and the organic UV filter includes about 9% to about 12% by weight of the homosalate and about 5% by weight of the octisalate based on the total weight of the composition.

10. The sunscreen composition according to claim 1, further comprising:
   d) at least one SPF booster.

11. The sunscreen composition according to claim 10, wherein the SPF booster is selected from the group consisting of ethylenediamine/stearyl dimer dilinoleate copolymer, butyloctyl salicylate, dimethicone and acrylates/dimethicone copolymer, a styrene/acrylates copolymer, and a silicone polymer comprising dimethicone and dimethicone/vinyl dimethicone crosspolymer, and combinations thereof.

12. The sunscreen composition according to claim 11, wherein the SPF booster comprises a silicone film former comprising ethylenediamine/stearyl dimer dilinoleate copolymer present from about 0.1% to about 5.0%, by weight based on the weight of the composition.

13. The composition according to claim 1, wherein the composition has an SPF of from about 30 to about 50.

14. The composition according to claim 1, wherein the composition has an SPF of about 40.

15. The composition according to claim 1, wherein PEG-40 stearate is present at about 1.5%, polysorbate 61 is present at about 1.75%, and sorbitan tristearate is present at about 1.25%, all amounts by weight based on the weight of the composition and wherein the composition has an SPF of 40.

16. The composition according to claim 1, wherein the at least one anionic emulsifier comprises potassium cetyl phosphate present at about 0.5% by weight based on the weight of the composition.

17. A sunscreen composition, comprising:
a metastable oil-in-water emulsion comprising aqueous and oil phases, the composition comprising:
   a) a UV filter system comprising:
      at least one mineral UV filter including about 12% by weight zinc oxide based on the total weight of the composition; and
      at least one organic UV filter including about 9% to about 12% by weight homosalate and about 5% by weight octisalate, based on the total weight of the composition;
   b) an emulsification system comprising:
      at least one ionic surfactant;
      at least one surfactant having a high HLB of greater than 9;
      at least one surfactant having a low HLB of 6 or less; and
      at least one anionic emulsifier;
   c) a solvent system comprising one or a combination of emollients and silicones; and
   d) at least one SPF booster,
wherein the UV filter system has a weight ratio of the at least one mineral UV filter to the at least one organic UV filter of about 1:1 to about 1:1.5,
wherein the composition has an SPF of about 40, and
wherein the composition is a flowable galenic suitable for spray application and
wherein the at least one surfactant having the high HLB includes PEG-40 stearate present at about 1.5%, polysorbate 61 present at about 1.75%, the at least one surfactant having the low HLB includes sorbitan tristearate present at about 1.25%, and the at least one anionic emulsifier includes potassium cetyl phosphate present at about 0.5%, all amounts by weight based on the weight of the composition.

18. A sunscreen composition, comprising:
a metastable oil-in-water emulsion comprising aqueous and oil phases, the composition comprising:
   a) a UV filter system comprising at least one mineral UV filter and at least one organic UV filter;
   b) an emulsification system comprising:
      at least one ionic surfactant;
      at least one surfactant having a high HLB of greater than 9;
      at least one surfactant having a low HLB of 6 or less; and
      at least one anionic emulsifier; and
   c) a solvent system comprising one or a combination of emollients and silicones, wherein the UV filter system has a weight ratio of the at least one mineral UV filter to the at least one organic UV filter of about 1:1 to about 1:1.5, and
wherein the at least one surfactant having the high HLB includes PEG-40 stearate, and polysorbate 61, the at least one surfactant having the low HLB includes sorbitan tristearate, the at least one anionic emulsifier includes potassium cetyl phosphate, and the emulsification system includes a ratio of the PEG-40 stearate and the polysorbate 61 to the sorbitan tristearate of about 2.6.

19. The composition according to claim 18, wherein PEG-40 stearate is present at about 1.5%, polysorbate 61 is present at about 1.75%, sorbitan tristearate is present at about 1.25%, and potassium cetyl phosphate is present at about 0.5%, all amounts by weight based on the weight of the composition.

20. The sunscreen composition according to claim 18, further comprising:
   d) at least one SPF booster selected from the group consisting of ethylenediamine/stearyl dimer dilinoleate copolymer, butyloctyl salicylate, dimethicone and acrylates/dimethicone copolymer, a styrene/acrylates copolymer, and a silicone polymer comprising dimethicone and dimethicone/vinyl dimethicone crosspolymer, and combinations thereof.

* * * * *